(12) United States Patent
Beilles et al.

(10) Patent No.: US 9,700,540 B2
(45) Date of Patent: Jul. 11, 2017

(54) DRONEDARONE FOR USE IN LEISHMANIASIS, FORMULATIONS AND ASSOCIATIONS FOR USE IN LEISHMANIASIS

(71) Applicant: SANOFI, Paris (FR)

(72) Inventors: Stephane Beilles, Paris (FR); Sandra Chambonnet, Paris (FR); Jean-Pierre Collaveri, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/012,810

(22) Filed: Feb. 1, 2016

(65) Prior Publication Data

US 2016/0151326 A1    Jun. 2, 2016

Related U.S. Application Data

(63) Continuation of application No. 14/402,587, filed as application No. PCT/EP2013/060513 on May 22, 2013, now abandoned.

(60) Provisional application No. 61/650,182, filed on May 22, 2012.

(30) Foreign Application Priority Data

Oct. 31, 2012   (EP) .................................... 12306362
Nov. 28, 2012   (EP) .................................... 12306472

(51) Int. Cl.
*A61K 31/34*    (2006.01)
*A61K 31/343*   (2006.01)
(Continued)

(52) U.S. Cl.
CPC .......... *A61K 31/343* (2013.01); *A61K 9/0014* (2013.01); *A61K 9/06* (2013.01);
(Continued)

(58) Field of Classification Search
CPC ................ A61K 31/343; A61K 31/685; A61K 31/7048; A61K 31/133; A61K 9/06;
(Continued)

(56) References Cited

U.S. PATENT DOCUMENTS

2002/0150622 A1    10/2002  Philbrook et al.
2011/0124724 A1*   5/2011   Gaudin ................ A61K 31/343
                                                          514/469

FOREIGN PATENT DOCUMENTS

EP          0471609 B1        8/1991
WO          02/051383 A2      7/2002
WO          2009/144551 A2   12/2009

OTHER PUBLICATIONS

Benaim et al, In Vitro Anti-Trypanosoma cruzi Activity of Dronedarone, a Novel Amiodarone Derivative with an Improved Safety Profile, Antimicrobial Agents Chemotherapy, Jul. 2012, vol. 56, No. 7 p. 3720-3725.*

(Continued)

*Primary Examiner* — T. Victor Oh
(74) *Attorney, Agent, or Firm* — McDonnell Boehnen Hulbert & Berghoff

(57) ABSTRACT

The invention relates to dronedarone or one of its pharmaceutically acceptable salts for the treatment of leishmaniasis, formulations and associations comprising dronedarone or one of its pharmaceutically acceptable salts for the treatment of leishmaniasis.

17 Claims, 3 Drawing Sheets

(51) Int. Cl.
   A61K 45/06    (2006.01)
   A61K 31/133   (2006.01)
   A61K 31/685   (2006.01)
   A61K 31/7048  (2006.01)
   A61K 9/00     (2006.01)
   A61K 9/06     (2006.01)
   A61K 47/36    (2006.01)
   A61K 47/10    (2017.01)
   A61K 47/14    (2017.01)
   A61K 9/107    (2006.01)
   A61K 47/38    (2006.01)

(52) U.S. Cl.
   CPC ............ *A61K 9/107* (2013.01); *A61K 31/133* (2013.01); *A61K 31/685* (2013.01); *A61K 31/7048* (2013.01); *A61K 45/06* (2013.01); *A61K 47/10* (2013.01); *A61K 47/14* (2013.01); *A61K 47/36* (2013.01); *A61K 47/38* (2013.01)

(58) Field of Classification Search
   CPC .... A61K 9/0014; A61K 9/0046; A61K 47/36; A61K 45/06
   USPC .................................................. 514/77, 467
   See application file for complete search history.

(56) References Cited

OTHER PUBLICATIONS

A.E. Paniz-Mondolfi et al. "Concurrent chaga's diseasee and borderline disseminated cutaneous Leishmanias : the role of amiodarone as an antitrypanosomatidae drug." Therapeutics and Clinical Risk Management, vol. 4(3), pp. 559-663, Jun. 2008.

Benaim Gustavo et al. "In Vitro Anti-Trypanosoma cruzi Activity of Dronedarone, a novel Amiodarone derivative with an improved safety profile." Antimocrobial Agents and Chemotherapy, vol. 56(7), pp. 3720-3725, Apr. 16, 2012.

Kathofer Sven et al. "The novel antiarrhythmic drug dronedarone: comparison with amiodarone." Cardiovascular Drug Reviews, vol. 23(3), pp. 217-230, Jan. 1, 2005.

Serrano-Martin Xenon et al. "Amiodarone and miltefosine act synergistically against Leishmania mexicana and can induce parasitological cure in a murine model of cutaneous Leishmaniasis." Antimicrobial Agents and Chemotherapy, vol. 53(12), pp. 5108-5113, Oct. 5, 2009.

International Preliminary Report on Patentability of the European Patent Office regarding International Application No. PCT/EP2013/060513, dated Nov. 26, 2014.

European Search Report of the European Patent Office regarding EP 12 30 6362, dated Dec. 20, 2012.

Audisio D. et al. "Synthesis and antikinetoplastid activities of 3-substituted quinolinones derivatives," European Journal of Medicinal Chemistry 52:44-50 (Mar. 16, 2012).

Frézard F. et al. "Pentavalent Antimonials: New Perspectives for Old Drugs," Molecules 14(7):2317-2336 (Jun. 30, 2009).

Odds, F.C. "Synergy, antagonism, and what the chequerboard puts between them," Journal of Antimicrobial Chemotherapy 52:1 (Jun. 12, 2003).

de Macedo-Silva et al., "Antiproliferative, Ultrastructural, and Physiological Effects of Amiodarone on Promastigote and Amastigote Forms of Leishmania amazonensis," Mol Biol Int. 2011:876021 (Jun. 13, 2011).

Piccini et al., "Comparative efficacy of dronedarone and amiodarone for the maintenance of sinus rhythm in patients with atrial fibrillation," J Am Coll Cardiol, 54(12):1089-95 (Sep. 15, 2009).

* cited by examiner

DRONEDARONE FOR USE IN LEISHMANIASIS, FORMULATIONS AND ASSOCIATIONS FOR USE IN LEISHMANIASIS

CROSS-REFERENCE TO RELATED APPLICATION

This application is a continuation of U.S. patent application Ser. No. 14/402,587, filed Nov. 20, 2014, which in turn is a national stage application under 35 U.S.C. §371 of International Application No. PCT/EP2013/060513, filed May 22, 2013, which claims priority to the U.S. Provisional App. No. 61/650,182, filed May 22, 2012, to European Patent Application No. 12306362.0, filed Oct. 31, 2012, and to European Patent Application No. 12306472.7, filed Nov. 28, 2012, the disclosures of which are explicitly incorporated by reference herein.

BACKGROUND OF THE INVENTION

Field of the Invention

The present invention relates to dronedarone or one of its pharmaceutically acceptable salts for the treatment of leishmaniasis, in particular cutaneous leishmaniasis with its various strains around the world, and/or leishmaniasis issued from *Leishmania amazonensis, Leishmania donovani*, or *Leishmania major* as well to formulation in particular topical formulation comprising dronedarone or one of its pharmaceutically acceptable salts, to their preparation and to their therapeutic application.

Description of the Related Art 2-n-Butyl-3-[4-(3-di-n-butylaminopropoxy)benzoyl]-5-methylsulphonamidobenzofuran, or dronedarone, and pharmaceutically acceptable salts thereof, in particular its hydrochloride salts, are described in European Patent EP 0 471 609 B1.

Moreover, dronedarone is indicated to reduce the risk of hospitalization for atrial fibrillation in patients in sinus rhythm with a history of paroxysmal or persistent atrial fibrillation (AF) or is indicated for the maintenance of sinus rhythm after successful cardioversion in adult clinically stable patients with paroxysmal or persistent atrial fibrillation (AF).

SUMMARY OF INVENTION

Surprisingly, the applicant has now showed that dronedarone may be used to treat leishmaniasis.

Especially, the applicant proposed formulations for topical administration that are suitable to treat leishmaniasis.

In fact, to be effective, such formulation should allow the penetration/liberation of the active principle in the layer of the skin where the parasites are located.

It would then be possible to obtain high concentrations of the active drug locally in the dermis, and avoiding high plasma concentration of the drug and associated systemic side effects.

One additional feature of such formulation is to avoid/reduce toxicity reactions of the skin on contact with the formulation.

Furthermore, association of dronedarone with others anti-leishmaniasis agents is possible and has several advantages such as decreasing the dose of administrated drugs to avoid side effects and avoid apparition of resistances to the chosen treatment with time.

Thus, the present invention relates to formulation in particular topical formulation comprising dronedarone or one of its pharmaceutically acceptable salts and at least a pharmaceutically acceptable excipient, to their preparation and to their therapeutic application such as treatment of leishmaniasis, in particular cutaneous leishmaniasis and/or leishmaniasis issued from *Leishmania amazonensis, Leishmania donovani* or *Leishmania major* strains.

DETAILED DESCRIPTION OF THE INVENTION

Figure 1:
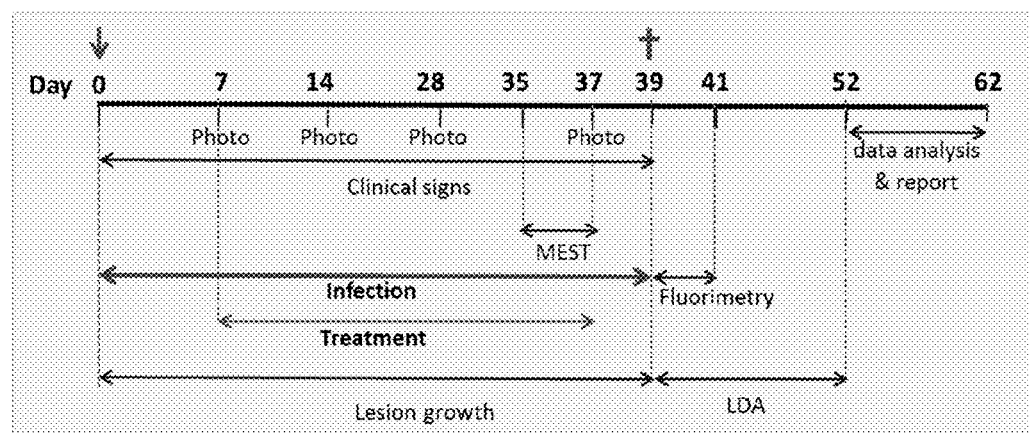
FIG. 1 illustrates the protocol timeline for procedure in Example 1.

The present invention relates to a pharmaceutical composition in particular for topical administration (topical pharmaceutical composition) comprising dronedarone or one of its pharmaceutically acceptable salts and at least a pharmaceutically acceptable excipient for topical administration, to their preparation and to their therapeutic application such as treatment of leishmaniasis, in particular cutaneous leishmaniasis and/or leishmaniasis issued from *Leishmania amazonensis, Leishmania donovani* or *Leishmania major* strains.

The present invention also relates to the use of dronedarone or one of its pharmaceutically acceptable salts for the preparation of a medicine for the treatment of leishmaniasis particularly cutaneous leishmaniasis and/or leishmaniasis issued from *Leishmania amazonensis, Leishmania donovani* or *Leishmania major* strains.

The present invention also relates to dronedarone or one of its pharmaceutically acceptable salts for use in the treatment of leishmaniasis particularly cutaneous leishmaniasis and/or leishmaniasis issued from *Leishmania amazonensis, Leishmania donovani* or *Leishmania major* strains.

Another object of the invention is also an association or one of its pharmaceutically acceptable salts and an anti-leishmaniasis agent. Said association is used for the treatment of leishmaniasis particularly cutaneous leishmaniasis and/or leishmaniasis issued from *Leishmania amazonensis, Leishmania donovani* or *Leishmania major* strains.

In one embodiment, said anti-leischmaniasis agent is selected among the following agents:
  Miltefosine or one of its pharmaceutically acceptable derivatives,
  Amphotericin B or one of its pharmaceutically acceptable derivatives,
  pentavalent antimonials derivatives such as meglumine antimoniate.

Said pharmaceutically acceptable salt of dronedarone is the hydrochloride salt.

In one embodiment, said leishmaniasis is issued from *Leishmania* strains resistant to pentavalent antimonials derivatives, and in particular *Leishmania amazonensis* strains, resistant to pentavalent antimonials derivatives in particular resistant to meglumine antimoniate.

It may be mentioned that formulations of meglumine antimoniate are notably commercialized under the trademark Glucantime®.

Said topical formulation or pharmaceutical composition may be a hydro-alcoholic gel, a semi-solid hydrophilic waxy formula, an oil in water or a water in oil emulsion particularly a hydro-alcoholic gel.

Said topical formulation or pharmaceutical composition may comprise an excipient such as hydroxypropyl methylcellulose (HPMC) in particular HPMC at 2% of the total weight of the formulation.

In one embodiment, said topical formulation or pharmaceutical composition may be a hydro-alcoholic gel comprising at least hydroxypropyl methylcellulose as excipient.

Said topical formulation or pharmaceutical composition wherein dronedarone or one of its pharmaceutically acceptable salt may be used in a proportion of 10% by weight of the active principle in base form.

Higher or lower dosages may be appropriate; these dosages are comprised within the scope of the present invention.

It may be mentioned that the term formulation or composition may be used indifferently.

The examples which follow describe the preparation of certain formulations in accordance with the invention. These examples are not limitative, and merely illustrate the present invention.

Example 1

Tests against cutaneous leishmaniasis were performed using the experimental model of BALB/c mouse infection with *Leishmania amazonensis*.

Formulations:

Formulations are prepared using techniques well known by one skilled in the art.

a) Dronedarone.

| Formulation 5 | Dronedarone | aqueous gel, [Dronedarone] = 10%, in 20 g vial |
| Formulation 6 | Dronedarone | semi solid hydrophilic waxy formula, [Dronedarone] = 110%, in 20 g vial |
| Formulation 7 | Dronedarone | oil in water emulsion, [Dronedarone] = 10%, in 20 g vial |

Formulations 5, 6 and 7 are detailed below:

| Formulation 5 (hydro-alcoholic gel = aqueous gel) | % |
| --- | --- |
| citrate buffer 0.5M pH 4.0 | 44 |
| Ethanol | 44 |
| HPMC | 2 |
| dronedarone | 10 (eq. base) |

| Formulation 6 (semi-solid hydrophilic waxy) | % |
| --- | --- |
| Lauroyl polyoxylglycerides (Gelucire 44/14) | 75 |
| Propylene glycol | 15 |
| dronedarone | 10 (eq. base) |

| Formulation 7 (oil in water emulsion*) | % |
| --- | --- |
| Anionic self-emulsifying base based on palmitostearate derivatives (SEDEFOS 75) | 8.1 |
| Soya oil | 22.5 |
| Glycerin | 59.4 |
| dronedarone | 10 (eq. Base) |

*Water is replaced by an hydrophilic excipient. Thus, the emulsion is constituted by droplets of oil dispersed in a hydrophilic matrix.

b) Control Glucantime Formulations:

Glucantime—PBS formulation #8: injectable formulation of Glucantime mixed with sterile PBS (20 mg/ml), stored at 4° C.

This preparation is equivalent to the commercial Glucantime®, identified by WHO as a first intention treatment for cutaneous leishmaniosis.

Procedures a) Protocol timelines are provided in FIG. 1.

b) Infection

Mice at 8 weeks of age were infected with 10 µl of $10^6$ promastigotes in the right ear pinna under light ether anesthesia.

c) Lesion Growth

Infected and non-infected contralateral ear thicknesses were measured every 3-4 days with a caliper gauge, and the lesion sizes were expressed as the difference between the thickness of infected and non-infected ears.

d) Treatment with Intra Lesional Glucantime and Topical Dronedarone

On day 7 of infection, animals were randomly separated at 5 animals/mouse cage (1 group of animals for each dronedarone or glucantime formulation). Another infected group was only for infection follow-up.

i) Topical treatment: Infected ears were treated with approx 20 mg of the appropriate topical dronedarone formulation once a day for 30 days. The formulations were collected from their original recipient with the tip of a disposable plastic spatula, and spread in the inner side of the infected pinna under a 10 secs-massage using the same spatula:

ii) Intralesional treatment: Infected ears were s.c. injected in the inner side of the infected ear with 10 µl of PBS containing 200 µg of powder Glucantime, twice a week from days 7 to 37 of infection (8 doses):

e) Cutaneous Sensitization (MEST):

Mouse Ear Swelling Test (MEST) can detect reliably moderate to strong sensitizers, as indicated by OECD guidelines for testing of chemicals. On day 34 of infection the contralateral non-infected ears were treated (challenged) with the correspondent Dronedarone formulation. Ear swelling was measured at various times after challenge (0 h, 1 h, 5 h, 24 h, 48 h and 72 h).

f) Clinical Signs:

Animals were weighted on days 0 of infection and at weekly periods, subsequently. The animals were observed daily, for signs of morbidity and death. Abnormal clinical signs during these routine checks were recorded. Clinical observations including mortality, monitoring of convulsions, lethargy, sleep, coma, salivation, diarrhea, cage side examination, skin color, fur, eyes and mucous membrane, spontaneous and voluntary motor activity and necropsy—in case the animal dies were recorded. Any unusual aspect of the treated lesions such as vesicles, complete ulceration, crust, darkening were also recorded. according to the international guidelines (WHO/OECD).

g) Pictures

Pictures from infected ears (treated and untreated) were taken with a digital camera at weekly intervals.

h) Parasite Load by Limiting Dilution Assay (LDA)

On day 39 of infection, animals were sacrificed under anesthesia and the infected ears were aseptically cleaned with iodinated ethanol followed by ethanol alone. The ears were cut off along its base and aseptically weighted. They were then individually cut into pieces, and single-cell suspensions were prepared in PBS containing antibiotics (1 ml/ear) using a stainless steel mesh (Sigma). The sieved tissues were gently pipetted up-down 8× for cell dissociation. The cell suspensions were pre-diluted 500× in medium M199 supplemented with 10% heat inactivated foetal calf serum, antibiotics 100 U/ml Penicillin/100 µg/ml streptomycin, 5 ug/ml hemine and 2% human urine), and then serially diluted 3-fold (50 µl+100 µl) in triplicates in flat-bottom micropates for a total of 24 dilutions. Microplates were incubated at 26° C. in a humidified BOD incubator. Wells were checked every 3-4 days for the presence of promastigotes for up to 20 days. The number of parasites in each infected ear was calculated according to the tissue mass and the last dilution theoretically containing 1 tissue amastigote.

Figure 2:
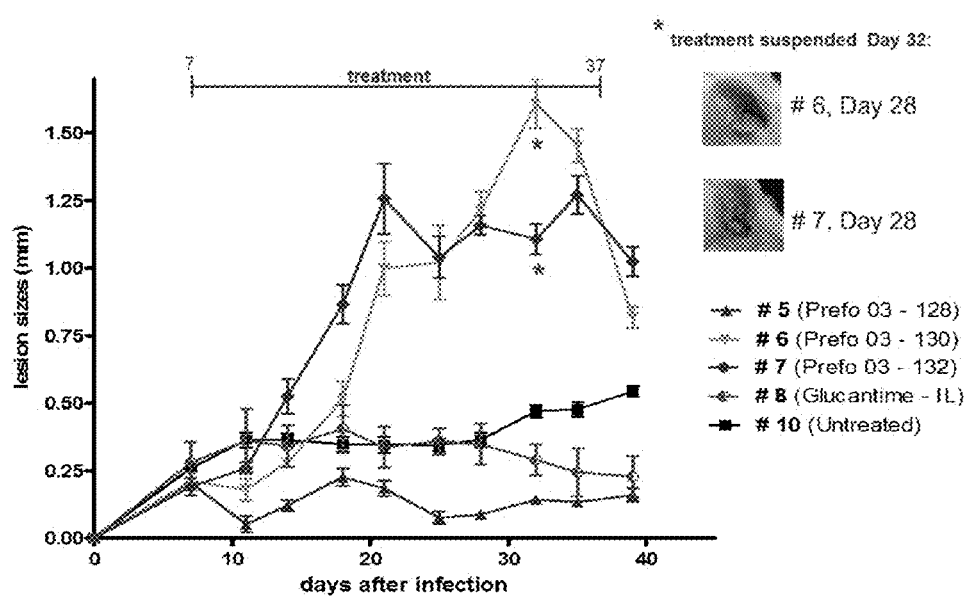
FIG. 2 illustrates lesion growth in Dronedarone-treated mice. Mice were infected on Day 0. Topical daily treatment started on Day 7 and continued until Day 37 with all the indicated Dronedarone formulations, except for Groups #6 and #7 which treatment was suspended on Day 32 due to toxicity (skin irritancy). The lesion sizes were measured at the indicated times (n=5).
Figure 3:
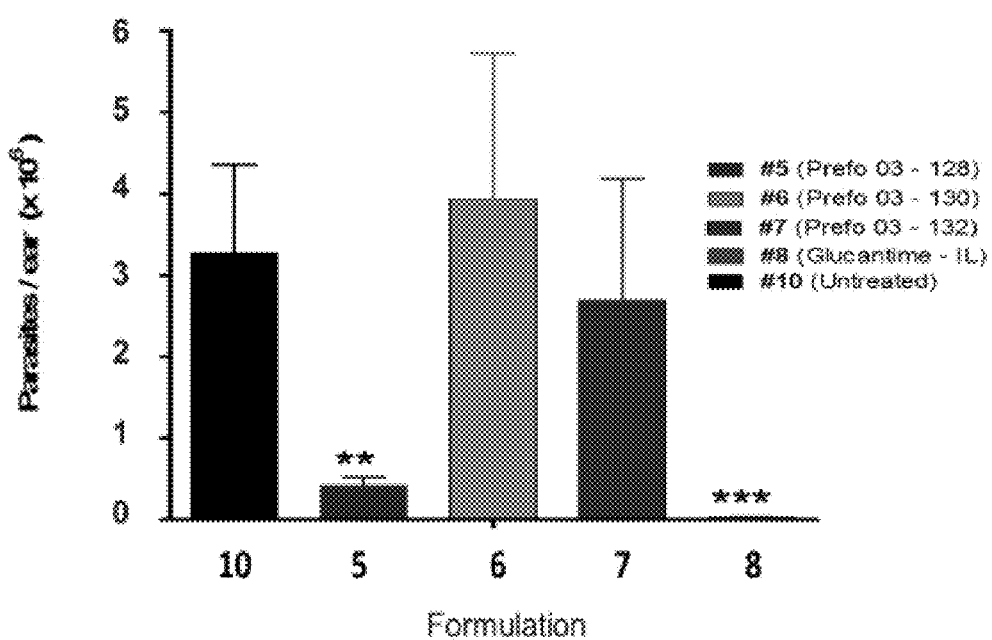
FIG. 3 shows parasite loads in dronedarone-treated mice. On day 39 of infection, the parasite loads in the ears of mice treated with the indicated formulations as for FIG. 2 were determined by Limiting Dilution Assay. Means±SD (n=5). $p<0.005$, *$p<0.001$.

Results on Efficacy of Dronedarone Formulations:

Dronedarone: Lesion growth: Formulation #5 (aqueous gel) was very effective throughout treatment, close to the reference treatment #8 (intralesional Glucantime) (FIG. 2). Formulations #6 (hydrophilic waxy semi-solid) and #7 (emulsion o/w) induced increased lesion sizes. This was due to skin irritancy (see MEST FIG. 11), not to promoted parasite growth (see FIG. 3). Besides, suspension of #6 and #7 treatments on day 32 led to rapid decrease of ear thicknesses: afterwards:

Dronedarone: Parasite loads in the ear. On day 39 of infection (30 days of treatment), the parasite loads in the ears were significantly lower in the group topically treated with #5 (aqueous gel). Formulations #6 (hydrophilic waxy semi-solid) and #7 (emulsion o/w) did not alter the parasite loads (FIG. 3).

Conclusions

The formulation 5 was the most promising in the control of lesion growth throughout the infection, the low parasite load at the end of the experiment was compatible with the controlled lesion growth, similar to achieved with 8 doses of 200 µg intralesional Glucantime. The animals looked happy throughout the treatment, gained weight normally and did not mount cutaneous sensitivity upon challenge.

Example 2

In vitro study of the efficacy of dronedarone on a strain of *Leishmania amazonensis*, in comparison with the reference treatments meglumine antimoniate, miltefosine, and amphotericin B in similar laboratory conditions.

A strain of *Leishmania amazonensis* (MHOM/BR/73/M2269) were used. Dronedarone hydrochloride and meglumine antimoniate were supplied by Sanofi. Amphotericin B (désoxycholate) and miltefosine were bought at Sigma-Aldrich.

The study concerned two cellular models:
1/Axenic amastigotes of *L. amazonensis* (isolated parasites)
2/Intramacrophagic amastigotes of *L. amazonensis* (parasites hosted in macrophages, as found in dermis, during the cutaneous Leishmaniosis infection).

The first cellular model which cultivates in a medium based on M199, allows defining the intrinsic activity of a substance on the parasite itself while the second cellular model integrates the capacity of the substance to cross the membrane of the macrophage and that of the phagolysosome. The used macrophages are cells RAW 264.7, which cultivate in medium based on DMEM with 10% of foetal serum of veal.

Determination of the IC50 of each of the molecules

Solutions of dronedarone in the DMSO, meglumine antimoniate and miltefosine in the water, and amphotericin B in an isotonic glucose solution (G5) were prepared before every experiment. The evaluations in vitro were the object of three independent experiments duplicate. The assays were realized by quantifying the parasitic DNA with the SYBR-GREEN as described by Audisio and al. (Eur. J. Med. Chem., 52: 44-50, 2012) as well as by qPCR for intramacrophagic amastigotes with amplification of the alpha-tubuline of the parasite. The results obtained with both methods are similar.

The inhibition concentration of 50% of the growth of the parasites (IC50) was determined after 72 hours of contact with dronedarone compared with meglumine antimoniate, miltefosine and amphotericin B, used as reference products.

On axenic amastigotes (test conditions 1/), dronedarone has a IC50 of 0.34±0.06 µM, while meglumine antimoniate has a IC50 of 908±159 µM, miltefosine a IC50 of 0.9±0.2 µM and amphotericin B a IC50 of 0.031±0.002 µM.

On intramacrophagic amastigotes (test conditions 2/), dronedarone has a IC50 of 0.50±0.22 µM, while meglumine antimoniate has a IC50 of 133.63±10.41 µM, miltefosine a IC50 of 1.87±0.032 µM and amphotericin B a IC50 of 0.047±0.005 µM.

Evaluation of the potential toxicity of dronedarone on human host cells (macrophages) compared to the reference drugs.

Study of the cytotoxicity on macrophages (cells RAW 264.7)

The non-toxic maximal concentration (CMA) was determined by the technique to the Blue Trypan according to has method described in Audisio and al. (Eur. J. Med. Chem., 52: 44-50, 2012).

The CMA of the dronedarone is 12.5 µM
The CMA of the meglumine antimoniate is >200 µM.
The CMA of the amphotericin B is 6.25 µM
The CMA of the miltefosine is 50 µM Then, the toxicity of dronedarone on the dermis macrophages is lower than most of the reference drugs, and will not impede its therapeutic use for cutaneous leishmaniasis.

Study of the association of dronedarone with meglumine antimoniate, miltefosine and amphotericin B Association of dronedarone with each of the reference products was studied according to the method described by Odds and al., J. Antimicrob. Chemother., 52:1, 2003, to identify a synergic or additive or antagonistic action. The study comprised three independent experiments which allowed the calculation of the Fractional Inhibitory Concentration Index (FICI):

If FICI<0.5: Synergy
If 0.5<FICI<4: additive Effect, no interaction
If FICI<4: antagonism Interaction between dronedarone and meglumine antimoniate:

On axenic amastigotes, FICI=0.27. A synergic effect between dronedarone and meglumine antimoniate was obtained.

On intramacrophagic amastigotes, FICI=0.79. An additive effect between dronedarone and meglumine antimoniate was obtained.

Interaction between the dronedarone and the miltefosine:

On axenic amastigotes, FICI=0.39. A synergy between dronedarone and miltefosine was obtained.

On intramacrophagic amastigotes, FICI=0.46. A synergy between dronedarone and miltefosine was obtained.

Interaction between dronedarone and amphotericin B:

On axenic amastigotes, FICI=0.63. An additive effect between dronedarone and amphotericin B was obtained.

On intramacrophagic amastigotes, FICI=0.54. An additive effect between dronedarone and amphotericin B was obtained.

Conclusions

A/activity of dronedarone on the parasites, as compared with reference drugs.

Dronedarone presents a strong activity anti-leishmaniasis in vitro on both models axenic amastigotes and intramacrophagic amastigotes of *Leishmania amazonensis*, with lower IC50 within the micromolar range, what places it between amphotericin B and miltefosine, in term of activity. The intrinsic activity on the parasite itself is thus maintained when this one is protected in the phagolysosome inside the macrophage.

B/activity of dronedarone on the parasites, in association with reference drugs:

The interaction of dronedarone with meglumine antimoniate or with amphotericin B is additive type. No antagonistic effect was demonstrated, what suggests that a concomitant use of dronedarone with meglumine antimoniate or amphotericin B may be possible.

The interaction of dronedarone with miltefosine is of synergic type suggests that a concomitant use of dronedarone with miltefosine may be of interest for example to decrease the administrated doses.

Example 3

In vitro study on *Leishmania amazonensis* strains resistant to meglumine antimoniate (Glucantime®)

On *Leishmania amazonensis* strains resistant to meglumine antimoniate (IC50=200 mM) under promastigote form, chemosensitivity to dronedarone is similar that one observed on strains that are not resistant to meglumine antimoniate (active principle of Glucantime®).

That means that the mechanism of action of dronedarone on the parasites differs from the one of glucantime. Dronedarone has a potential to treat Glucantime resistant strains as found e.g. in Latin America.

Example 4

In vitro study on building of resistance to Dronedarone with time, using *Leishmania amazonensis* strain.

The test consists in long term culture of a *L. amazonensis* strain (promastigote form), in contact with increasing doses of dronedarone, starting with initial concentrations lower than the IC50.

At regular timepoints, the viability and pathogenicity of parasites is confirmed with moving the culture to axenic amastigotes and intramacrophagic amastigotes, and calculating the new inhibitive concentration for 50% of the population (IC50).

After six months of culture and exposition of the parasites to dronedarone, no significant modification of the inhibitory concentration (IC50) was observed.

As a reference: a similar exposition of the strain to Glucantime has brought to an increase of the IC50×200.

While the study will be continued for a while, it can already be stated that the molecule does not generate a resistance in exposed parasites.

Example 5

In Vitro Study on *Leishmania donovani* and *Leishmania major*

As to evaluate the polyvalence of dronedarone as a treatment on the various strains of *Leishmania* spread around the world, with known various sensitivities to the reference drugs, the previous tests were completed with strains considered as representative of the various zones of endemy.

Strains of *Leishmania donovani* (MHOM/ET/67/HU3) and *Leishmania major* (MHOM/SU/73/5-ASKH) were used for this study.

Dronedarone hydrochloride and the meglumine antimoniate were supplied by Sanofi. Miltefosine was bought at Sigma-Aldrich.

The study in vitro concerned four cellular models:

1/Axenic amastigotes of *L. donovani* and *L. major* (isolated parasites)

2/Intramacrophagic amastigotes of *L. donovani* and *L. major* (parasites hosted in macrophages, as found in dermis, during the cutaneous Leishmaniosis infection).

The model of axenic amastigotes is cultivated in a medium based on M199 and allows defining the intrinsic activity of a substance on the parasite itself while the model of intramacrophagic amastigotes integrates the capacity of the substance to cross the membrane of the macrophage and that of the phagolysosome.

The used macrophages are cells RAW 264.7, which cultivate in a medium based on DMEM with 10% of foetal serum of veal.

Determination of the IC50 of dronedarone, Glucantime® and of miltefosine:

The solutions of dronedarone in the DMSO, meglumine antimoniate and miltefosine in the water, were prepared before every experiment. The evaluations in vitro were the object of three independent experiments.

The assays were realized by quantifying the parasitic DNA with the SYBRGREEN as described by Audisio and al. (Eur. J. Med. Chem., 52: 44-50, 2012).

The inhibition concentration of 50% of the growth of the parasites (IC50) was determined after 72 hours of contact with dronedarone compared with meglumine antimoniate and miltefosine, used as reference products.

On the axenic amastigotes of *L. donovani*, dronedarone has a IC50 of 47.38±6.27 µM, while meglumine antimoniate has a IC50>1000 mM, and miltefosine a IC50 of 13.0±1.25 µM.

On *L. major's* axenic amastigotes, dronedarone has a IC50 of 2.55±0.51 µM, while meglumine antimoniate has a IC50>1000 µM, and miltefosine a IC50 of 5.57±1.50 µM.

On the intramacrophagic amastigotes of *L. donovani*, dronedarone has a IC50 of 1.67±0.10 µM, while meglumine antimoniate has a IC50 of 390.36±40.46 µM, and miltefosine a IC50 of 0.88±0.10 µM.

On *L. major's* intramacrophagic amastigotes, dronedarone has a IC50 of 1.32±0.12 µM, while meglumine antimoniate has a IC50 of 347.98±79.87 µM, and miltefosine a IC50 of 0.72±0.11 µM.

Besides, dronedarone does not present toxicity for macrophages to the concentration of 12.5 μM. Its cytotoxic concentration 50% (CC50) is thus superior to 12.5.

Conclusions

1—in vitro activity of the dronedarone on *Leishmania donovani* (as a model of Indian/African strains)

The dronedarone presents a strong activity on intramacrophagic amastigotes of *L. donovani* similar to that of miltefosine, of the order of 1-2 μM, while it is weakly active on axenic amastigotes. The therapeutic index of dronedarone defined as the CC50 on intramacrophagic amastigotes of *L. donovani*/IC50 is thus superior to 7.

2—in vitro activity of the dronedarone on *Leishmania major* (as a model of middle east strains)

The dronedarone presents a strong activity in vitro on the models of axenic amastigotes and intramacrophagic amastigotes of *Leishmania major*, with IC50 lower than 3 μM, what places it at a level of activity similar to that of miltefosine. The intrinsic activity on the parasite itself is thus maintained when this one is protected in the phagolysosome inside the macrophage. The therapeutic index of the dronedarone defined as the CC50 on intramacrophagic amastigotes of *L. major*/IC50 is thus superior to 9.

These results tend to demonstrate that dronedarone has a capacity to bring a therapeutic effect on various strains (3 models tested from around the world), at concentrations similar to miltefosine, and much lower than glucantime.

The invention claimed is:

1. A method of treating leishmaniasis, comprising topically administering a hydro-alcoholic gel formulation comprising dronedarone or one of its pharmaceutically acceptable salts.

2. The method according to claim 1, wherein the leishmaniasis is cutaneous leishmaniasis.

3. The method according to claim 1, wherein the leishmaniasis is caused by *Leishmania amazonensis* strains.

4. The method according to claim 1, wherein the leishmaniasis is caused by *Leishmania amazonensis* strains resistant to pentavalent antimonials.

5. The method according to claim 4 wherein said *Leishmania amazonensis* strain is resistant to meglumine antimoniate.

6. The method according to claim 1, wherein the leishmaniasis is caused by *Leishmania donovani* strains.

7. The method according to claim 1, wherein the leishmaniasis is caused by *Leishmania major* strains.

8. The method according to claim 1, wherein said pharmaceutically acceptable salt is dronedarone hydrochloride.

9. The method according to claim 1, wherein said formulation comprises at least one pharmaceutically acceptable excipient.

10. The method according to claim 9, wherein said pharmaceutically acceptable excipient is hydroxypropyl methylcellulose.

11. The method according to claim 1, wherein the dronedarone or one of its pharmaceutically acceptable salts is used in a proportion of 10% by weight of the active principle in base form.

12. The method according to claim 1, wherein the dronedarone or one of its pharmaceutically acceptable salts is administered in combination therapy with an anti-leischmaniasis agent.

13. The method according to claim 12, wherein the leishmaniasis is cutaneous leishmaniasis.

14. The method according to claim 12, wherein the leishmaniasis is caused by *Leishmania amazonensis* strains.

15. The method according to claim 12, wherein the leishmaniasis is caused by *Leishmania amazonensis* strains resistant to pentavalent antimonials.

16. The method according to claim 12 wherein said anti-leischmaniasis agent is selected among the following agents:

Miltefosine, Amphotericin B, and pentavalent antimonials.

17. The method according to claim 16 wherein said anti-leischmaniasis agent is meglumine antimoniate.

* * * * *